United States Patent
Shields et al.

(10) Patent No.: US 11,666,399 B2
(45) Date of Patent: Jun. 6, 2023

(54) ROBOTIC SURGICAL INSTRUMENT INCLUDING INSTRUMENT ROTATION BASED ON TRANSLATION POSITION

(71) Applicant: Covidien LP, Mansfield, MA (US)

(72) Inventors: Elizabeth Gayle Shields, Somerville, MA (US); Chi Min Seow, New Haven, CT (US); Jaimeen Kapadia, Cambridge, MA (US); Eric J. Taylor, Southington, CT (US); Richard S. Lech, Hamden, CT (US); Mark Hamilton MacLeod, Southbury, CT (US); Michael Zemlok, Prospect, CT (US); Vipul Agarwal, Brookline, MA (US)

(73) Assignee: COVIDIEN LP, Mansfield, MA (US)

( * ) Notice: Subject to any disclaimer, the term of this patent is extended or adjusted under 35 U.S.C. 154(b) by 443 days.

(21) Appl. No.: 16/759,189

(22) PCT Filed: Nov. 28, 2018

(86) PCT No.: PCT/US2018/062699
§ 371 (c)(1),
(2) Date: Apr. 24, 2020

(87) PCT Pub. No.: WO2019/108564
PCT Pub. Date: Jun. 6, 2019

(65) Prior Publication Data
US 2020/0323597 A1   Oct. 15, 2020

Related U.S. Application Data

(60) Provisional application No. 62/592,450, filed on Nov. 30, 2017.

(51) Int. Cl.
*A61B 34/35* (2016.01)
*A61B 46/10* (2016.01)
(Continued)

(52) U.S. Cl.
CPC .......... *A61B 34/35* (2016.02); *A61B 17/0686* (2013.01); *A61B 17/072* (2013.01);
(Continued)

(58) Field of Classification Search
CPC ..... A61B 34/35; A61B 46/10; A61B 17/0686; A61B 17/072; A61B 17/29; A61B 2017/00477
(Continued)

(56) References Cited

U.S. PATENT DOCUMENTS 8,636,192 B2   1/2014   Farascioni et al.
8,828,023 B2   9/2014   Neff et al.
(Continued)

FOREIGN PATENT DOCUMENTS

CA       2809745 A1     12/1996
CN    106 361 433 A      2/2017
(Continued)

OTHER PUBLICATIONS

Australian Examination Report for application No. 2018375307 dated Dec. 10, 2020.
(Continued)

*Primary Examiner* — Carl H Layno
*Assistant Examiner* — Michael J Lau
(74) *Attorney, Agent, or Firm* — Carter, DeLuca & Farrell LLP

(57) ABSTRACT

A robotic surgical system includes a slide rail, a surgical instrument, and a robotic surgical assembly. The robotic surgical assembly is coupled to the slide rail and translatable along the slide rail between a first position and a second position. The robotic surgical assembly is coupled to the surgical instrument. The robotic surgical assembly, or a portion thereof, is configured to automatically rotate to a predetermined orientation relative to the slide rail when the
(Continued)

robotic surgical assembly is disposed at the first position to enable the surgical instrument to be selectively uncoupled from the robotic surgical assembly.

19 Claims, 11 Drawing Sheets

(51) Int. Cl.
　　*A61B 17/068* (2006.01)
　　*A61B 17/072* (2006.01)
　　*A61B 17/29* (2006.01)
　　*A61B 17/00* (2006.01)

(52) U.S. Cl.
　　CPC .............. *A61B 17/29* (2013.01); *A61B 46/10* (2016.02); *A61B 2017/00477* (2013.01)

(58) Field of Classification Search
　　USPC ........................................................ 600/301
　　See application file for complete search history.

(56) References Cited

U.S. PATENT DOCUMENTS

| | | | |
|---|---|---|---|
| 8,925,786 B2 | 1/2015 | Holsten et al. | |
| 9,524,022 B2 | 12/2016 | Nakayama | |
| 2005/0215983 A1 | 9/2005 | Brock | |
| 2009/0024141 A1* | 1/2009 | Stabler ................... | A61B 34/30 606/130 |
| 2009/0024142 A1 | 1/2009 | Ruiz Morales | |
| 2014/0066944 A1 | 3/2014 | Taylor et al. | |
| 2014/0166023 A1* | 6/2014 | Kishi ..................... | A61B 90/50 128/849 |
| 2014/0350726 A1* | 11/2014 | Tsusaka .................. | B25J 13/02 700/257 |
| 2015/0257841 A1* | 9/2015 | Dachs, II ............... | A61B 34/30 403/321 |
| 2016/0157941 A1* | 6/2016 | Anvari ................... | A61B 34/70 279/143 |
| 2017/0281365 A1* | 10/2017 | Robinson ........... | A61B 17/0206 |

FOREIGN PATENT DOCUMENTS

| | | |
|---|---|---|
| EP | 3621544 A1 | 3/2020 |
| JP | 2013034833 A | 2/2013 |
| JP | 2013034862 A | 2/2013 |
| JP | 2013138965 A | 7/2013 |
| JP | 2019519288 A | 7/2019 |
| WO | 2015088647 A1 | 6/2015 |
| WO | 2017053358 A1 | 3/2017 |
| WO | 2017142738 A1 | 8/2017 |

OTHER PUBLICATIONS

Japanese Office Action for application No. 2020-529150 dated May 10, 2021 with English Translation.
Supplemental European Search Report dated Jul. 16, 2021.
India Examination Report for application No. 202017019483 dated Mar. 29, 2022 with English translation.
Australian Examination Report for application No. 2021200761 dated Mar. 4, 2022.
Chinese Office Action for application No. 201880077061.4 dated Nov. 14, 2022 with English translation.

* cited by examiner

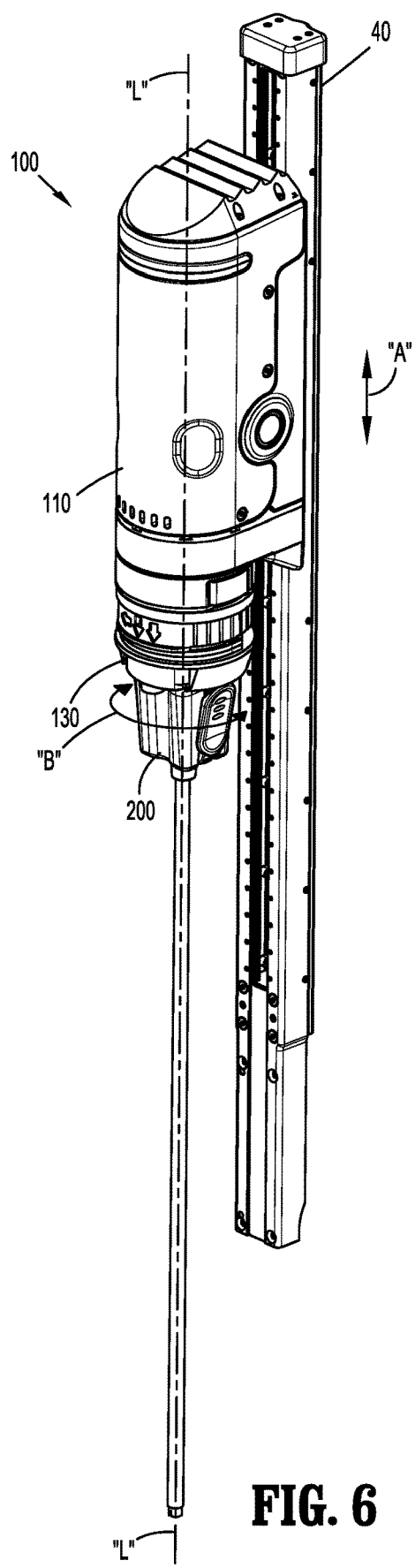
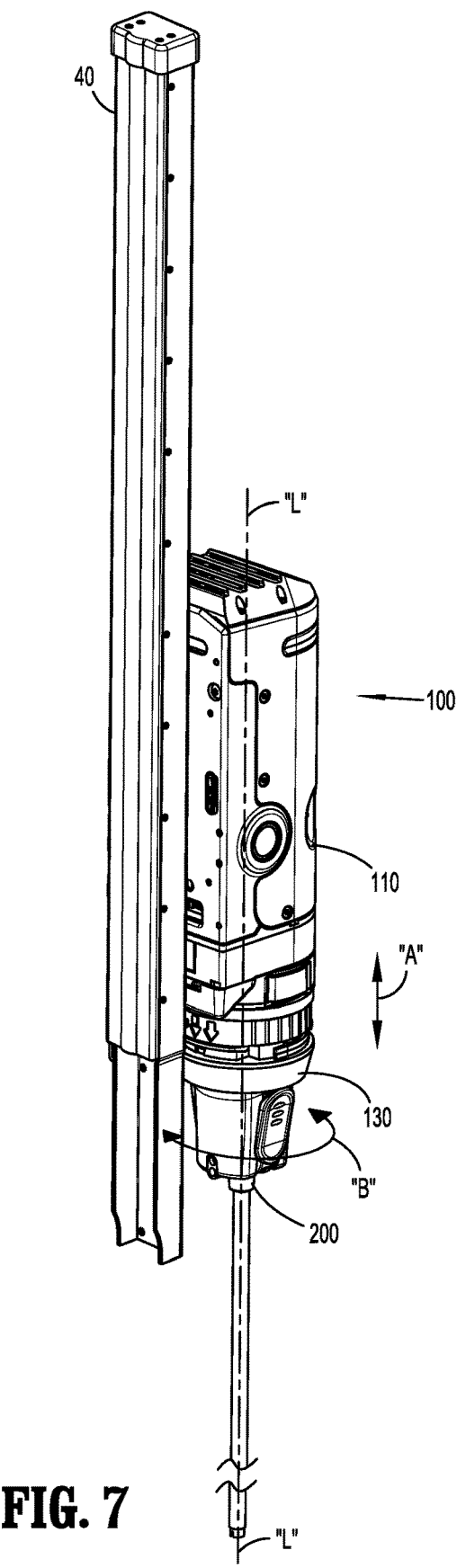
FIG. 6  FIG. 7

ROBOTIC SURGICAL INSTRUMENT INCLUDING INSTRUMENT ROTATION BASED ON TRANSLATION POSITION

CROSS-REFERENCE TO RELATED APPLICATIONS

This application is a U.S. National Stage Application filed under 35 U.S.C. § 371(a) of International Patent Application Serial No. PCT/US2018/062699, filed Nov. 28, 2018, which claims the benefit of and priority to U.S. Provisional Patent Application Ser. No. 62/592,450, filed Nov. 30, 2017, the entire disclosure of which is incorporated by reference herein.

BACKGROUND

Robotic surgical systems have been used in minimally invasive medical procedures. Some robotic surgical systems include a console supporting a surgical robotic arm and a surgical instrument having at least one end effector (e.g., a forceps or a stapling device) mounted to the robotic arm. The robotic arm provides mechanical power to the surgical instrument for its operation and movement. Each robotic arm may include an instrument drive unit that is operatively connected to the surgical instrument. The surgical instruments may include cables that are motor driven to operate end effectors of the surgical instruments.

SUMMARY

The present disclosure relates to robotic surgical systems used to conduct minimally invasive surgical procedures. The present disclosure provides for instrument rotation based on translation position.

In accordance with an aspect of the present disclosure, robotic surgical system includes a slide rail, a surgical instrument, and a robotic surgical assembly. The robotic surgical assembly is coupled to the slide rail and translatable along the slide rail between a first position and a second position. The robotic surgical assembly is coupled to the surgical instrument. The robotic surgical assembly, or a portion thereof, is configured to rotate to a predetermined orientation relative to the slide rail when the robotic surgical assembly is disposed at the first position to enable the surgical instrument to be selectively uncoupled from the robotic surgical assembly.

In some embodiments, the robotic surgical assembly may be configured to rotate automatically to the predetermined orientation relative to the slide rail.

In embodiments, movement of the robotic surgical assembly to the predetermined orientation may position the surgical instrument relative to the slide rail such that the surgical instrument can be uncoupled from the robotic surgical assembly via side-unloading.

In certain embodiments, the robotic surgical assembly may include an instrument drive unit and a sterile interface module coupled to the instrument drive unit. The surgical instrument may be selectively coupled to the sterile interface module. The surgical instrument may include a housing and the sterile interface module may include a semi-annular cuff. The semi-annular cuff may be positioned to receive the housing of the surgical instrument via side-loading to couple the surgical instrument to the sterile interface module. The semi-annular cuff may define a U-shaped opening that opens distally and laterally through the sterile interface module and may be configured to slidably receive a proximal portion of the housing of the surgical instrument therein to side-load the proximal portion of the housing into the U-shaped opening. The lateral opening of the U-shaped opening may be clear of the slide rail when the robotic surgical assembly is translated to the first position and rotated (e.g., the sterile interface module) into the predetermined orientation.

In some embodiments, rotation of the robotic surgical assembly may be robotically controlled as the robotic surgical assembly translates between the first position and the second position. One or more of the sterile interface module or the instrument drive unit may become freely rotatable once the robotic surgical assembly is rotated to the predetermined orientation.

In certain embodiments, the robotic surgical system may include a controller configured to electrically communicate with the robotic surgical assembly to enable the robotic surgical assembly (e.g., the sterile interface module) to rotate to the predetermined orientation when the robotic surgical assembly is disposed in the first position. The controller may be configured to selectively prevent the robotic surgical assembly from translating relative to the slide rail when the robotic surgical assembly is disposed in the first position.

In embodiments, the first position may be located at a proximal end portion of the slide rail and the second position may be located at a distal end portion of the slide rail.

According to another aspect of the present disclosure, a method for removing a surgical instrument from a robotic surgical assembly is provided. The method includes positioning the robotic surgical assembly at a predetermined location along a slide rail, rotating at least a portion of the robotic surgical assembly relative to the slide rail when the robotic surgical assembly is disposed at the predetermined location, positioning a lateral opening of the robotic surgical assembly so that the lateral opening is clear of the slide rail, and side-unloading the surgical instrument from the lateral opening.

The method may include automatically rotating at least a portion of the robotic surgical assembly relative to the slide rail when the robotic surgical assembly is disposed at the predetermined location.

Positioning the lateral opening of the robotic surgical assembly may include rotating a sterile interface module of the robotic surgical assembly. Rotating the sterile interface module may include positioning the lateral opening at a predetermined orientation relative to the slide rail.

Side-unloading the surgical instrument from the lateral opening may include sliding a housing of the surgical instrument along a semi-annular cuff of the sterile interface module.

Positioning the lateral opening at a predetermined orientation relative to the slide rail may include facing the lateral opening away from the slide rail.

The method may further include freely rotating the sterile interface module once the lateral opening is disposed in the predetermined orientation. The method may further include preventing the sterile interface module from axially translating along the slide rail while enabling the sterile interface module to freely rotate.

Positioning the robotic surgical assembly at the predetermined location along the slide rail may include retracting the robotic surgical assembly proximally along the slide rail to the predetermined location. Positioning the robotic surgical assembly at the predetermined location along the slide rail may include disposing the robotic surgical assembly at a proximal-most location along the slide rail.

Other aspects, features, and advantages provided by some or all of the illustrative embodiments described herein will be apparent from the description, the drawings, and the claims that follow.

BRIEF DESCRIPTION OF THE DRAWINGS

The accompanying drawings, which are incorporated in and constitute a part of this specification, illustrate embodiments of the present robotic surgical systems and, together with a general description of the disclosure given above, and the detailed description of the embodiment(s) given below, serve to explain the principles of the disclosure, wherein:

FIG. 6 is a front, perspective view of the robotic surgical assembly of FIG. 2, supported on a slide rail of the robotic surgical system of FIG. 1 and coupled to an embodiment of the various electromechanical surgical instruments of FIG. 2 while disposed in a first position along the slide rail;

FIG. 7 is a rear, perspective view of the robotic surgical assembly and electromechanical surgical instrument of FIG. 6 while disposed in a second position along the slide rail;

DETAILED DESCRIPTION

Figure 1:
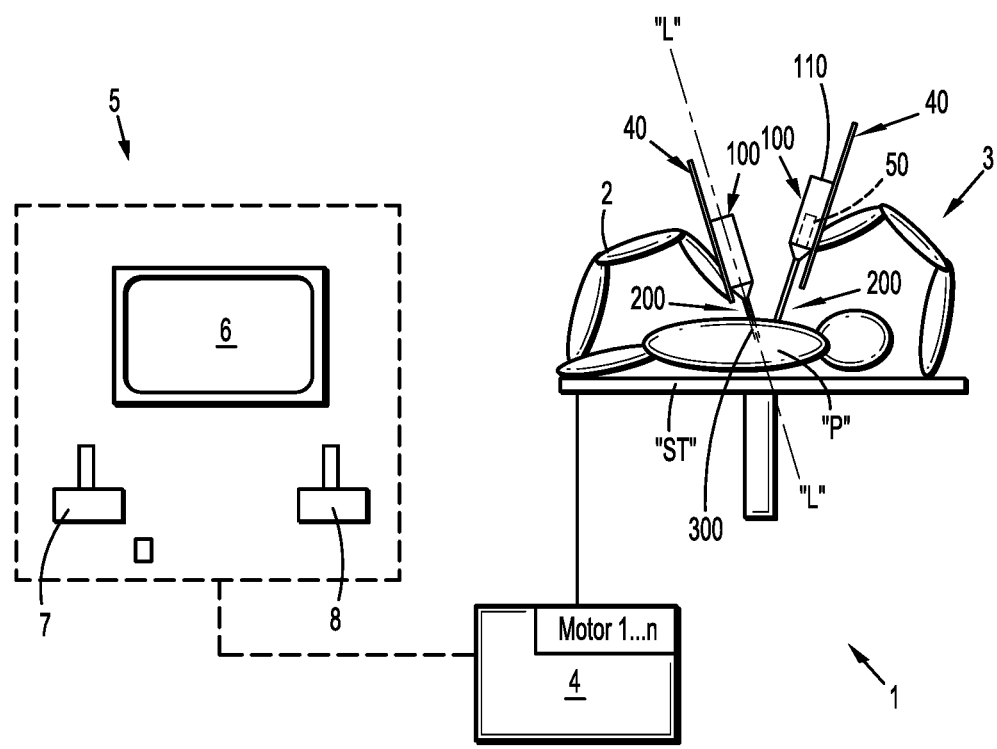
FIG. 1 is a schematic illustration of a robotic surgical system in accordance with the present disclosure.

Embodiments of the present robotic surgical systems are described in detail with reference to the drawings, in which like reference numerals designate identical or corresponding elements in each of the several views. As used herein, the term "distal" refers to structure that is closer to a patient, while the term "proximal" refers to structure farther from the patient.

As used herein, the term "clinician" refers to a doctor, nurse, or other care provider and may include support personnel. In the following description, well-known functions or constructions are not described in detail to avoid obscuring the present disclosure in unnecessary detail.

Referring initially to FIG. 1, a surgical system, such as, for example, a robotic surgical system 1, generally includes one or more surgical robotic arms 2, 3, a controller 4, and an operating console 5 coupled with controller 4. Any of the surgical robotic arms 2, 3 may have a robotic surgical assembly 100 and one or more electromechanical surgical instruments 200, 200',200" (FIG. 2) selectively couplable thereto, and which may include surgical staplers, graspers, endoscopes, etc. Electromechanical surgical instrument 200, for example, is a surgical stapler including an end effector 300 disposed at a distal portion thereof. In embodiments, robotic surgical assembly 100 is slidably attached to a slide rail 40 of one or more of surgical robotic arms 2, 3. In certain embodiments, robotic surgical assembly 100, or portions thereof, may be removably attached to slide rail 40 of one or more of surgical robotic arms 2, 3.

Operating console 5 of robotic surgical system 1 includes a display device 6, which is set up to display three-dimensional images; and manual input devices 7, 8, by means of which a clinician (not shown), is able to telemanipulate the robotic arms 2, 3 of robotic surgical system 1 in a first operating mode, as known in principle to a person skilled in the art. Each robotic arm of robotic arms 2, 3 may be composed of any number of members, which may be connected through any number of joints. Robotic arms 2, 3 may be driven by electric drives (not shown) that are connected to controller 4. Controller 4 (e.g., a computer) of robotic surgical system 1 is set up to activate the drives, for example, by means of a computer program, in such a way that robotic arms 2, 3, the attached robotic surgical assembly 100, and thus an attached electromechanical surgical instrument such as electromechanical surgical instrument 200 (including end effector 300) of robotic surgical system 1, execute a desired movement according to a movement defined by means of manual input devices 7, 8. Controller 4 may be set up in such a way that it regulates movement of robotic arms 2, 3 and/or of the drives.

Robotic surgical system 1 is configured for use on a patient "P" positioned (e.g., lying) on a surgical table "ST" to be treated in a minimally invasive manner by means of a surgical instrument, e.g., electromechanical surgical instrument 200 and, more specifically, end effector 300 of electromechanical surgical instrument 200. Robotic surgical system 1 may include more than two robotic arms 2, 3, the additional robotic arms are likewise connected to controller 4 and telemanipulatable by means of operating console 5. A surgical instrument, for example, electromechanical surgical instrument 200 (including end effector 300 thereof), may also be attached to any additional robotic arm(s).

Controller 4 of robotic surgical system 1 may control one or more motors (not shown), each motor configured to drive movement of robotic arms 2, 3 in any number of directions.

For a detailed discussion of the construction and operation of a similar robotic surgical system having one or more of the same or similar components for use with one or more components of the presently described robotic surgical system, reference may be made to U.S. Pat. No. 8,828,023, the entire disclosure of which is incorporated by reference herein.

Figures 2, 3:
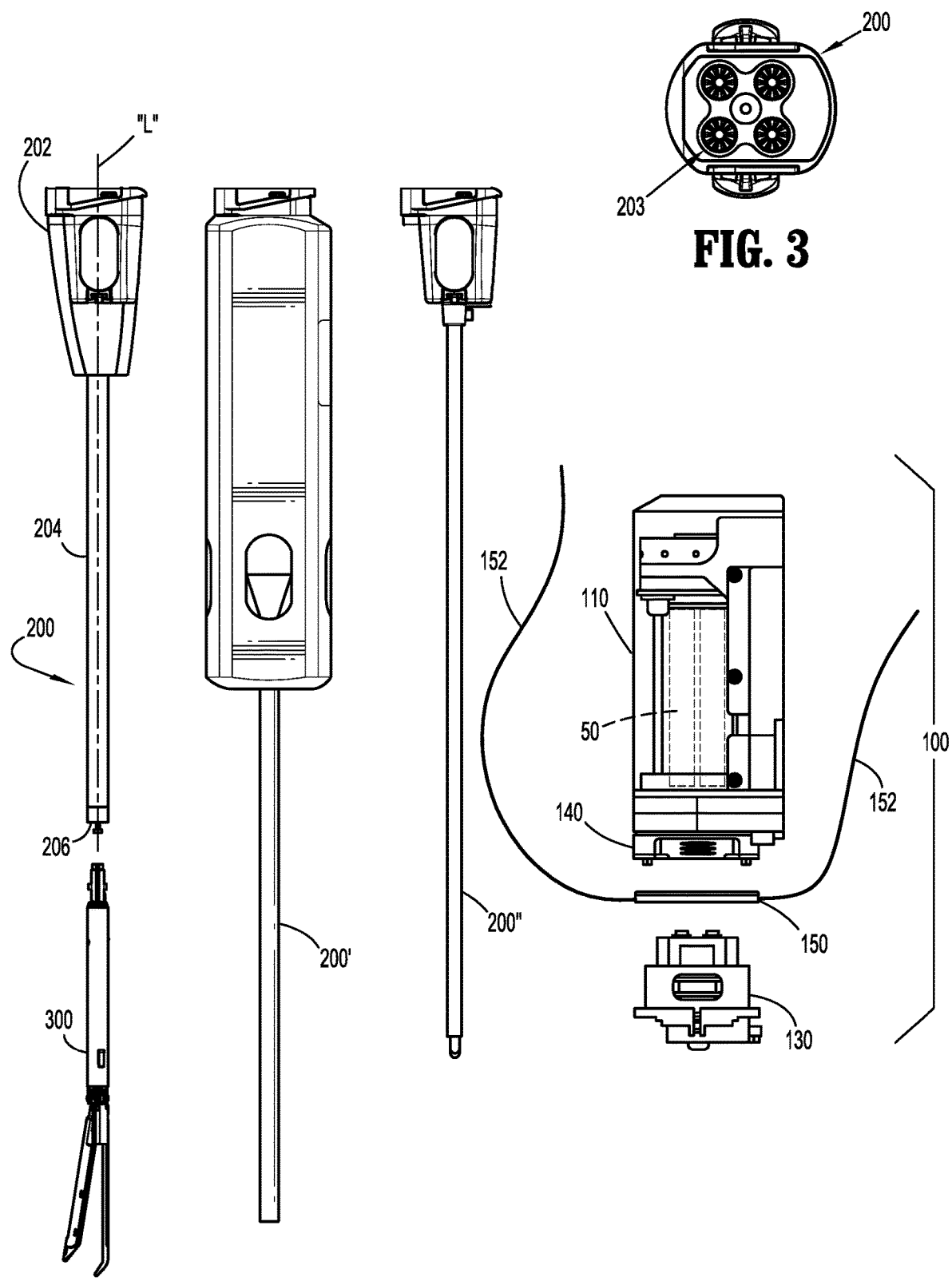
FIG. 2 is a side, elevational view, with parts separated, of a robotic surgical assembly of the robotic surgical system of FIG. 1 and embodiments of various electromechanical surgical instruments for use with the robotic surgical assembly.
FIG. 3 is a top view of one embodiment of the various electromechanical surgical instruments shown in FIG. 2.

Turning now to FIGS. 2 and 3, robotic surgical assembly 100 of robotic surgical system 1 includes an instrument drive unit 110 and a connector assembly 140. Instrument drive unit 110 supports one or more motors (e.g., a motor assembly or motor pack) 50 that may be controlled by controller 4. Motors 50 drive various operations of, for example, end effector 300 of electromechanical surgical instrument 200. Motors 50 may include a rotation motor, such as, for example, a canister motor. One or more of motors 50 (or a different motor, not shown) may be configured to drive a rotation of an attached electromechanical surgical instrument, or components thereof, relative to a longitudinal axis "L-L" thereof (e.g., electromechanical surgical instrument 200 seen in FIG. 1). Motors 50 can be configured to effect operation and/or movement of electromechanical end effector 300 of electromechanical surgical instrument 200, for example. Reference may be made to commonly owned International Patent Application No. PCT/US 14/61329, U.S. Pat. No. 8,636,192, or U.S. Pat. No. 8,925,786, the entire disclosures of each of which are incorporated by reference herein, for a detailed discussion of illustrative examples of the construction and operation of end effectors for use with, or connection to, the presently disclosed electromechanical surgical instruments.

Figure 4:
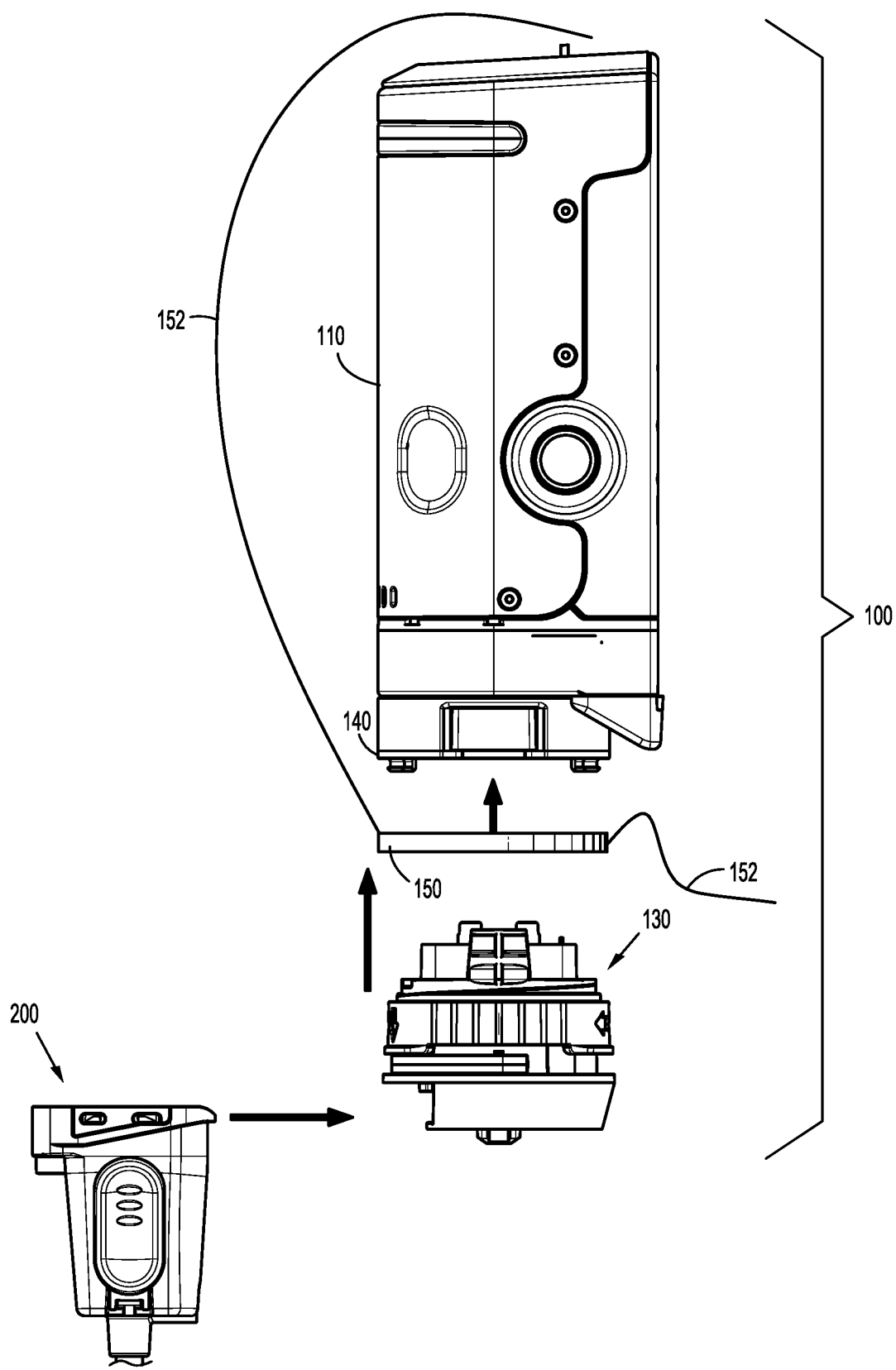
FIG. 4 is a side, elevational view, with parts separated, of the robotic surgical assembly of FIG. 2.

As seen in FIGS. 2 and 4, robotic surgical assembly 100 of robotic surgical system 1 further includes a ring member 150 having a sterile drape 152 secured thereto. Ring member 150 of robotic surgical assembly 100 is configured for attachment to instrument drive unit 110 of robotic surgical assembly 100 to enable sterile drape 152 of robotic surgical assembly 100 to overlie robotic surgical assembly 100 and the robotic arms 2, 3. Ring member 150 can be seated (e.g., passively) between instrument drive unit 110 and sterile interface module 130. In some embodiments, ring member 150 may be configured for rotatable attachment to a distal end of connector assembly 140 (e.g., via snap fit). Sterile drape 152 can be arranged as desired about the instrument drive unit 110, robotic surgical assembly 100, and robotic arms 2, 3 to provide a sterile barrier between the various aforementioned components and/or the surgical site/fluids and electromechanical surgical instruments, such as surgical instruments 200 (e.g., stapler), 200' (e.g., endoscope), and/or 200" (e.g., grasper).

Figure 5:
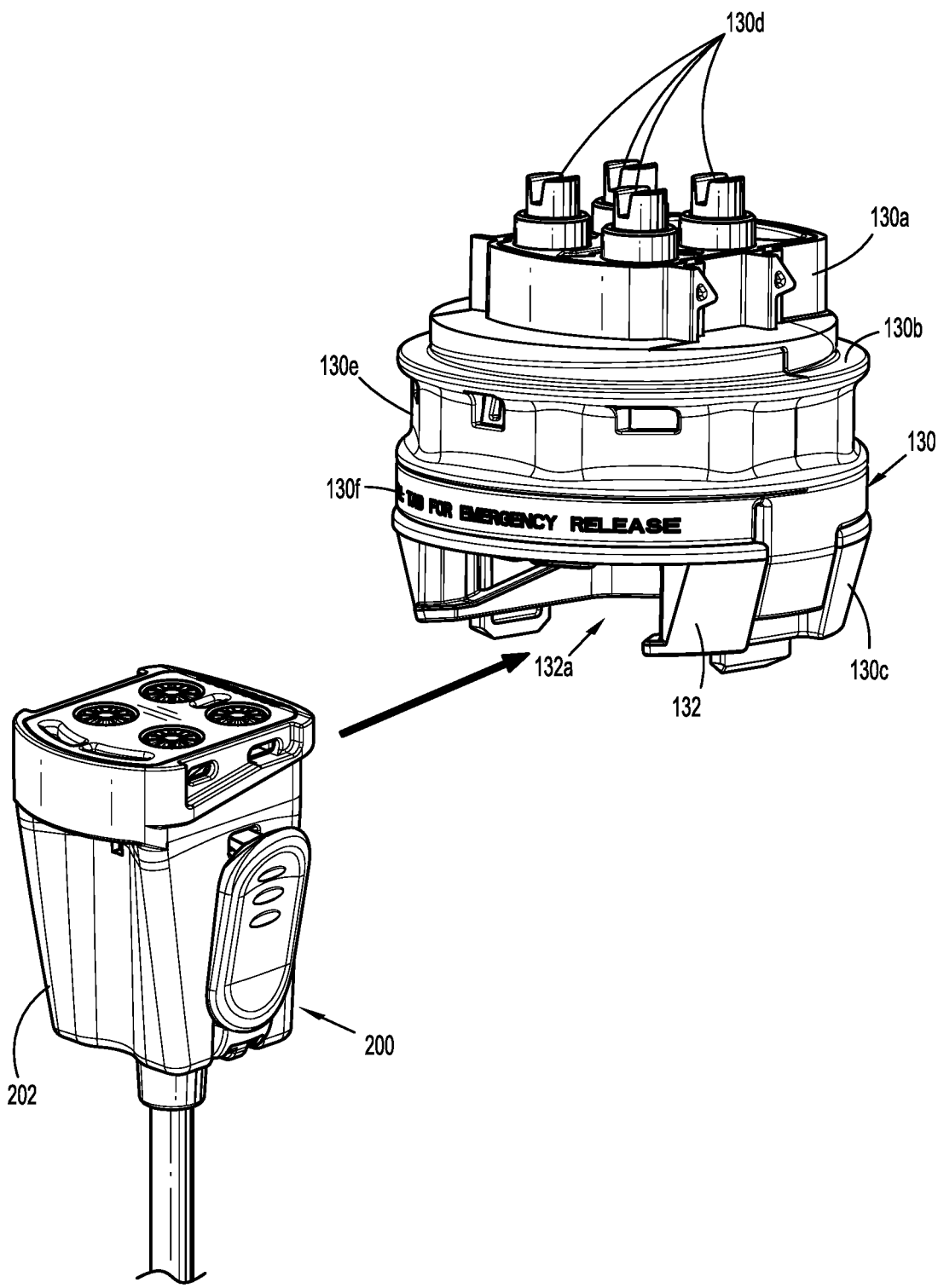
FIG. 5 is a perspective view, with parts separated, illustrating an embodiment of the various electromechanical surgical instruments of FIG. 2 being side-loaded onto a sterile interface module of the robotic surgical assembly of FIG. 2.

With reference to FIGS. 2, 4, and 5, robotic surgical assembly 100 of robotic surgical system 1 also includes a sterile interface module 130 provided for selectively interconnecting robotic surgical assembly 100 and any one of electromechanical surgical instruments 200, 200', and/or 200" of robotic surgical system 1. Such electromechanical surgical instruments may be selectively side-loaded and/or unloaded from robotic surgical assembly 100 via sterile interface module 130 (see, e.g., FIGS. 4 and 5).

Sterile interface module 130 of robotic surgical assembly 100 generally includes an upper portion 130a, an intermediate portion 130b, and a lower portion 130c that support one or more drive assemblies 130d for transferring forces through sterile interface module 130. Upper portion 130a of sterile interface module 130 selectively couples sterile interface module 130 to instrument drive unit 110 of robotic surgical assembly 100. Intermediate portion 130b movably supports a decoupling collar 130e and a release ring 130f that provide a manual override function for manually releasing the electromechanical surgical instrument (e.g., unclamping the electromechanical surgical instrument from tissue) so that the electromechanical surgical instrument, such as electromechanical surgical instrument 200, may be removed from the patient. Lower portion 130c includes a semi-annular cuff 132 that defines a U-shaped opening 132a. U-shaped opening 132a of sterile interface module 130 opens distally and laterally through sterile interface module 130 for slidably receiving a housing (see e.g., housing 202 of FIG. 2) of one of the electromechanical surgical instruments 200, 200', and/or 200" of robotic surgical system 1. For a more detailed description of sterile interface module 130 and side-loading and/or unloading of an electromechanical surgical instrument onto/from a sterile interface module, reference can be made to International Publication No. WO/2017/053358, the entire disclosure of which is incorporated by reference herein.

In general, sterile interface module 130 of robotic surgical assembly 100 functions to provide an interface between instrument drive unit 110 of robotic surgical assembly 100 and an electromechanical surgical instrument, such as electromechanical surgical instrument 200, of robotic surgical system 1. This interface advantageously maintains sterility, provides a means to transmit electrical communication between robotic surgical assembly 100 and the attached electromechanical surgical instrument, provides a means for transferring rotational force from robotic surgical assembly 100 to the attached electromechanical surgical instrument for performing a function with the attached electromechanical surgical instrument, and/or provides a means to selectively attach/remove electromechanical surgical instruments to/from robotic surgical assembly 100 (e.g., for rapid instrument exchange).

With continued reference to FIG. 2, electromechanical surgical instrument 200 of robotic surgical system 1 includes a housing 202 at a proximal end portion thereof and an elongated shaft 204 that extends distally from housing 202. Elongated shaft 204 of electromechanical surgical instrument 200 includes a wrist assembly 206 supported on a distal end portion of elongated shaft 204 that couples end effector 300 of electromechanical surgical instrument 200 to elongated shaft 204. Housing 202 of electromechanical surgical instrument 200 is configured to selectively couple to instrument drive unit 110 of robotic surgical assembly 100 (for example, via side-loading on a sterile interface module 130 of robotic surgical assembly 100) to enable motors 50 of instrument drive unit 110 of robotic surgical assembly 100 to operate end effector 300 of electromechanical surgical instrument 200.

As seen in FIGS. 1 and 3, housing 202 of electromechanical surgical instrument 200 supports a drive assembly 203 that mechanically and/or electrically cooperates with motors 50 of instrument drive unit 110 of robotic surgical assembly 100 to enable surgical instrument 200 and/or end effector 300 thereof to perform one or more functions such as articulation, rotation, and/or firing.

Turning now to FIGS. 6-13, in use, with electromechanical surgical instrument 200 coupled to robotic surgical assembly 100 of robotic surgical system 1, controller 4 of robotic surgical system 1 electrically communicates with robotic surgical assembly 100 to selectively translate robotic surgical assembly 100 (and thereby electromechanical surgical instrument 200) relative to slide rail 40 between a first translation position (FIG. 6) and a second translation position (FIG. 7), as indicated by arrows "A". Controller 4 also electrically communicates with robotic surgical assembly 100 to selectively rotate at least portions of robotic surgical assembly 100 (e.g., sterile interface module 130) about longitudinal axis "L-L," as indicated by arrows "B" (and thereby rotate electromechanical surgical instrument 200).

Figure 8:
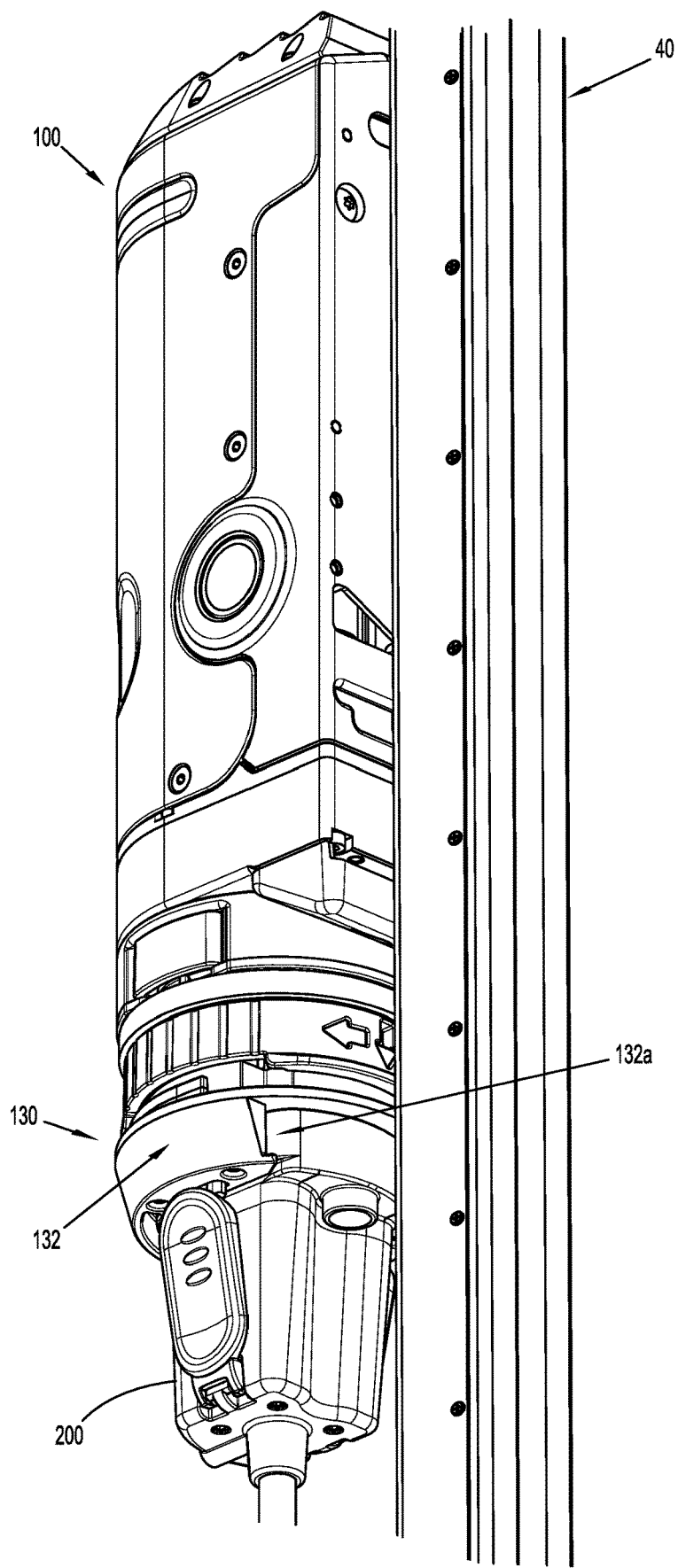
FIG. 8 is an enlarged, rear, bottom, perspective view of a portion of FIG. 6.
Figure 11:
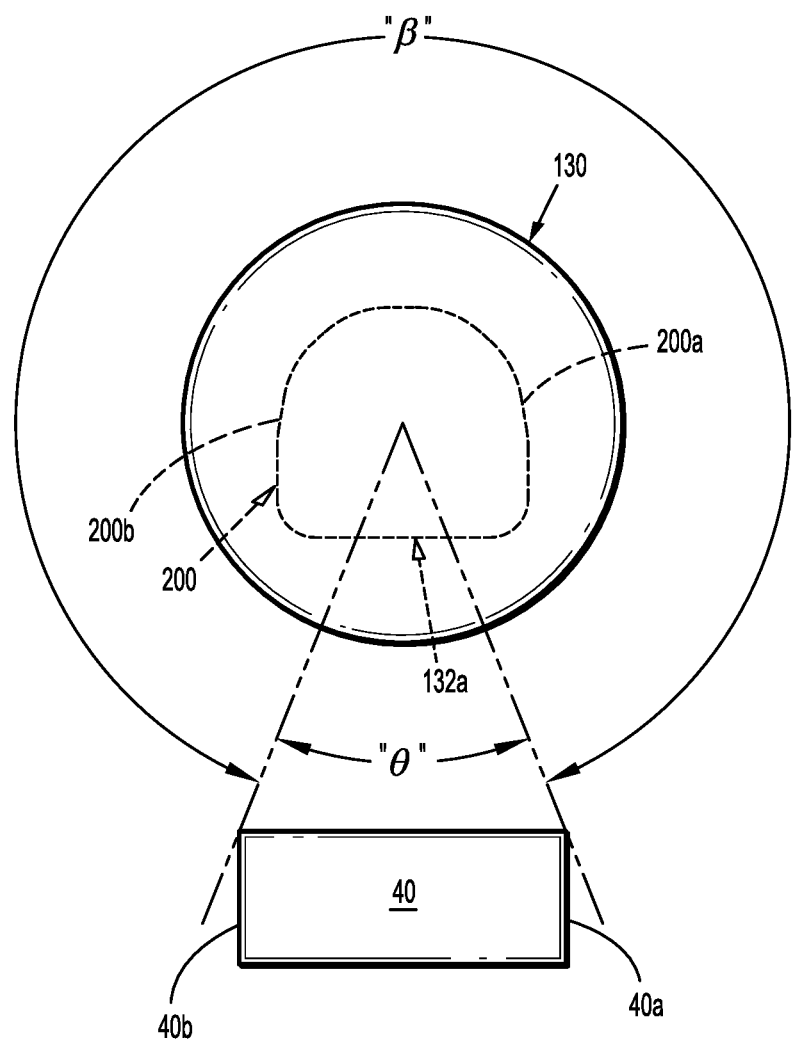
FIG. 11 is a schematic, top view illustrating rotational orientations of the sterile interface module relative to the slide rail while the sterile interface module is coupled to an embodiment of the various electromechanical surgical instruments of FIG. 2.

As illustrated in FIGS. 8 and 11, during operation, such rotation of robotic surgical assembly 100 and electromechanical surgical instrument 200 of robotic surgical system 1 can cause semi-annular cuff 132 of sterile interface module 130 of robotic surgical assembly 100 to be positioned such that lateral opening 132a of sterile interface module 130 at least partially faces slide rail 40 and inhibits side-unloading of electromechanical surgical instrument 200 from sterile interface module 130. Such inhibited positioning of lateral opening 132a/electromechanical surgical instrument 200 is illustrated via a blocking angle "Θ", shown in FIG. 11, which may be about 15 degrees, for example, and defined between opposed outer side surfaces 40a, 40b of slide rail 40. Blocking angle "Θ" may increase or decrease (from between about 0 degrees to about 180 degrees), depending upon a width of slide rail 40, a width of lateral opening 132a of sterile interface module 130, a width of housing 202 of electromechanical surgical instrument 200, etc. For instance, the greater the width of slide rail 40, the greater the blocking angle "Θ" will be, and vice versa.

With continued reference to FIG. 11, complementary to blocking angle "Θ," uninhibited positioning of lateral opening 132a/electromechanical surgical instrument 200 is illustrated via a clearance angle "β," shown in FIG. 11, which is the explement of blocking angle "Θ" (e.g., 345 degrees) such that blocking angle "Θ" and clearance angle "β" are explementary angles (e.g., they add up to 360 degrees). Clearance angle "β" is the explement angle through which electromechanical surgical instrument 200 can be freely coupled to, and/or uncoupled from, sterile interface module 130 without interference from slide rail 40. More particularly, when both of opposed outer side surfaces 200a, 200b of electromechanical surgical instrument 200 and lateral opening 132a of sterile interface module 130 are completely disposed within clearance angle "β," electromechanical surgical instrument 200 can be freely coupled to, and/or uncoupled from, sterile interface module 130 without interference from slide rail 40.

Figure 9:
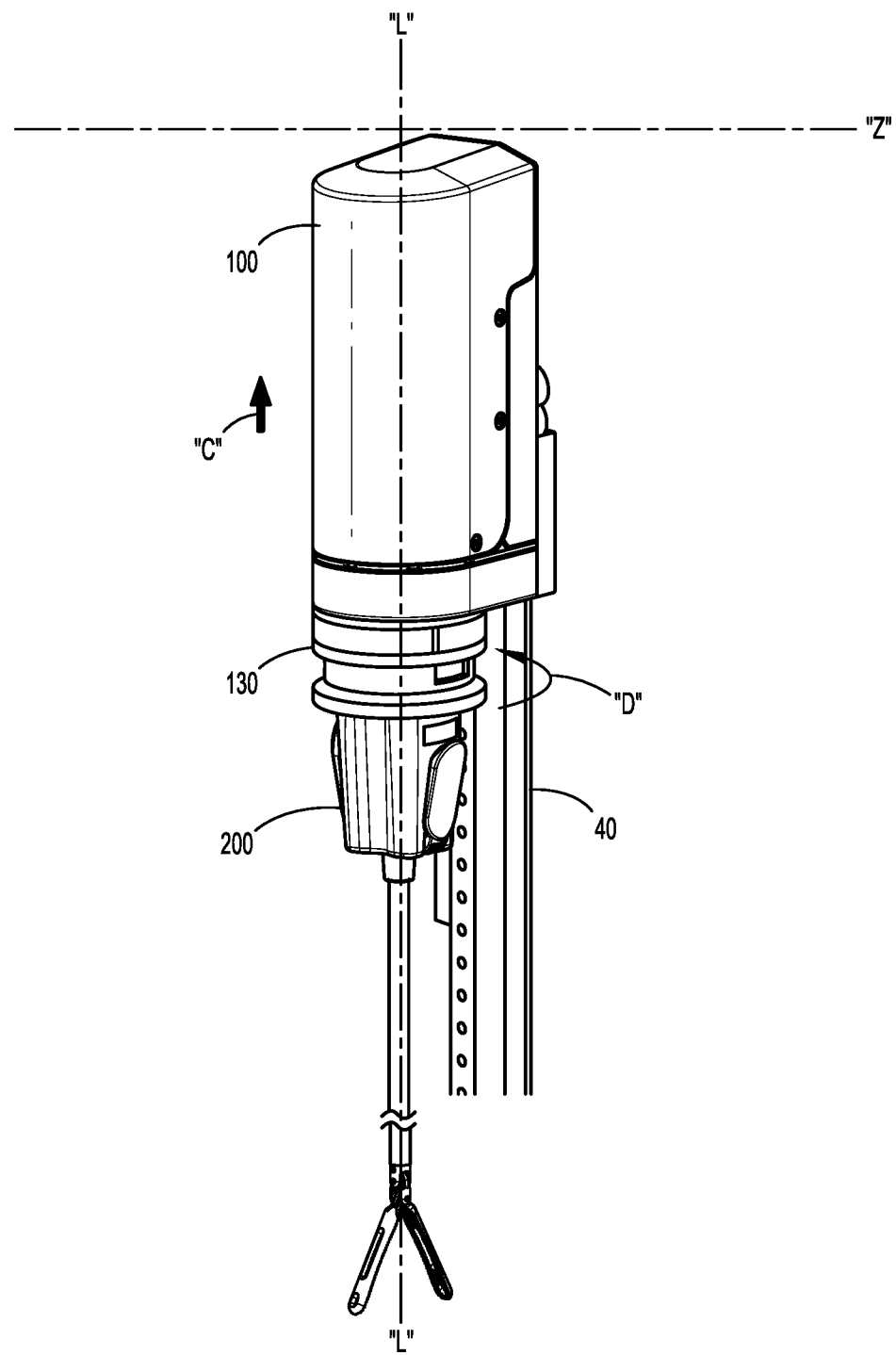
FIG. 9 is a front, perspective view of the robotic surgical assembly and electromechanical surgical instrument of FIG. 6 while disposed in a third position along the slide rail.
Figure 10:
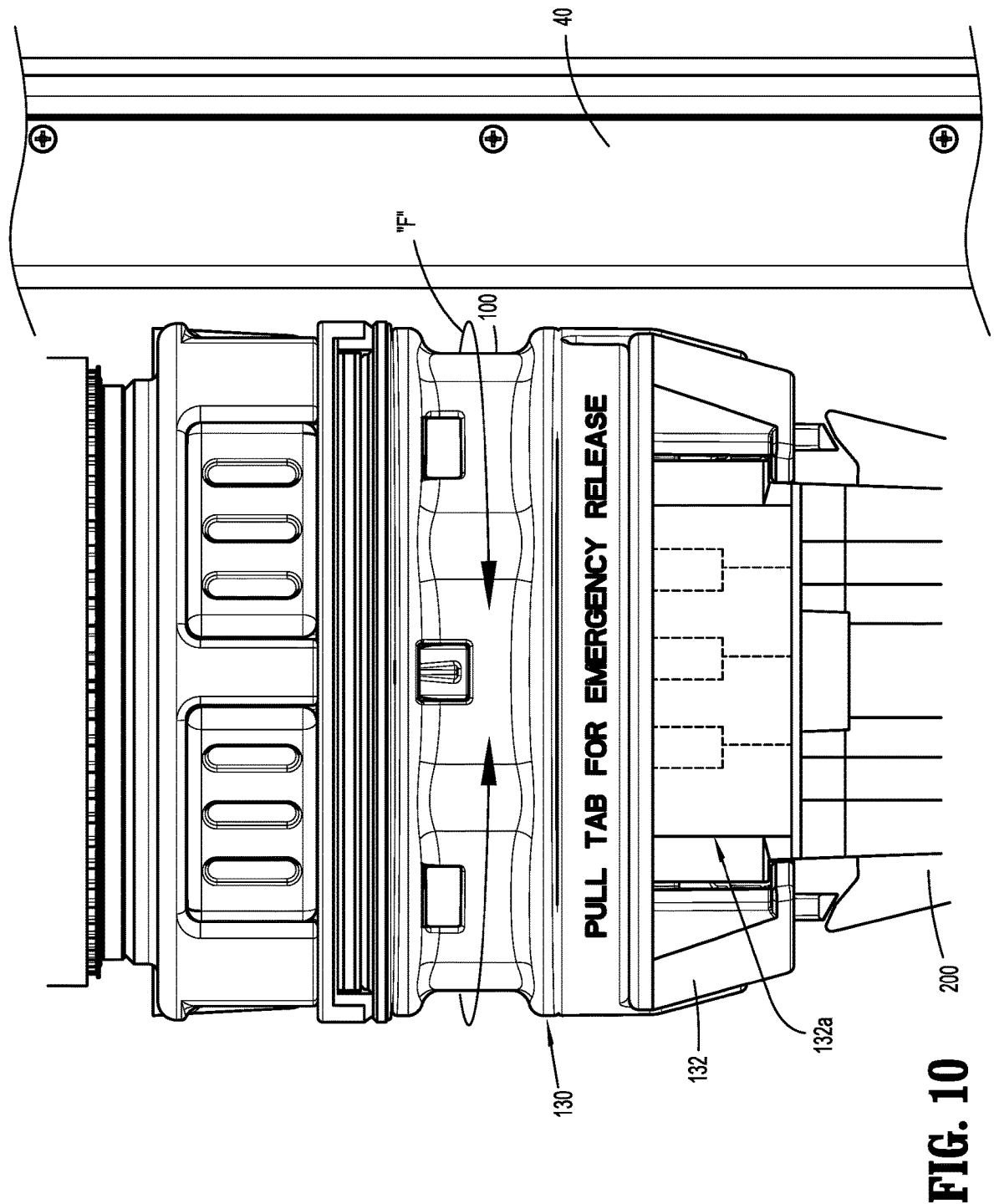
FIG. 10 is an enlarged, side, elevational view showing the sterile interface module of FIG. 5 and an embodiment of the various electromechanical surgical instruments of FIG. 2 disposed in a predetermined orientation relative to the slide rail.

With reference to FIGS. 9 and 10, to enable side-unloading of attached electromechanical surgical instrument 200 from sterile interface module 130 of robotic surgical assembly 100, robotic surgical assembly 100 is retracted proximally relative to slide rail 40, as indicated by arrow "C," to a third position (e.g. a predetermined proximal position) on slide rail 40, as indicated by plane "Z." In the third position of robotic surgical assembly 100, controller 4 of robotic surgical system 1 causes (e.g., automatically without input from manual input devices 7, 8) at least a portion of robotic surgical assembly 100 (e.g., sterile interface module 130) to rotate about longitudinal axis "L-L" of robotic surgical assembly 100, as indicated by arrows "D," toward a predetermined orientation (FIG. 10). The third position of robotic surgical assembly 100 may be a fully (and/or partially) retracted (or unretracted/advanced) position of robotic surgical assembly 100 relative to slide rail 40. The third position of robotic surgical assembly 100 may be proximal (or distal) to the first and second translation positions of robotic surgical assembly 100 described above. In some embodiments, the third position may be a proximal-most position (and/or distal-most position and/or some intermediate position) of robotic surgical assembly 100 relative to slide rail 40 that acts as a hard stop (e.g., for calibration). Such retraction and rotation can be effectuated by actuation of manual input devices 7, 8 (FIG. 1) (e.g., actuation of button thereon—not shown) of robotic surgical system 1, whereby release of actuation of manual input devices 7, 8 can enable sterile interface module 130 and electromechanical surgical instrument 200 of robotic surgical system 1 to be freely rotatable once sterile interface module 130 and electromechanical surgical instrument 200 are moved (e.g., fully retracted and rotated) to the predetermined orientation.

In some embodiments, slide rail 40, robotic surgical assembly 100, and/or components thereof, may include one or more sensors (not shown) disposed at one or more locations therealong to determine a position of robotic surgical assembly 100, or portions thereof, relative to slide rail 40. Such sensors may be any suitable sensor or device such as a microswitch, a Hall Effect switch, an encoder, a magnetic transducer, etc., or combinations thereof.

Figure 12:
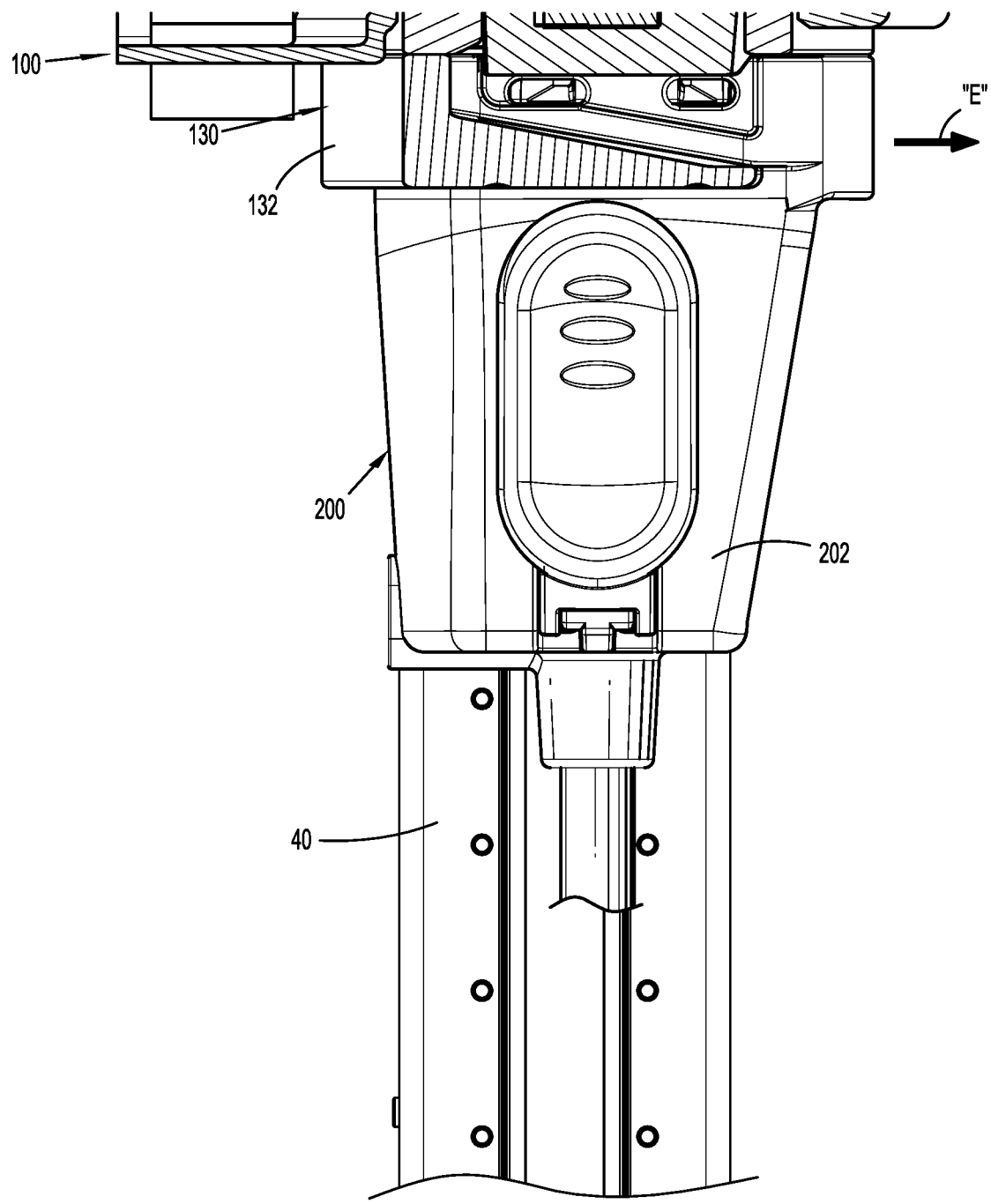
FIGS. 12 and 13 are progressive, partial cross-sectional views illustrating an embodiment of the various electromechanical surgical instruments of FIG. 2 being side-unloaded from the sterile interface module of FIG. 5.
Figure 13:
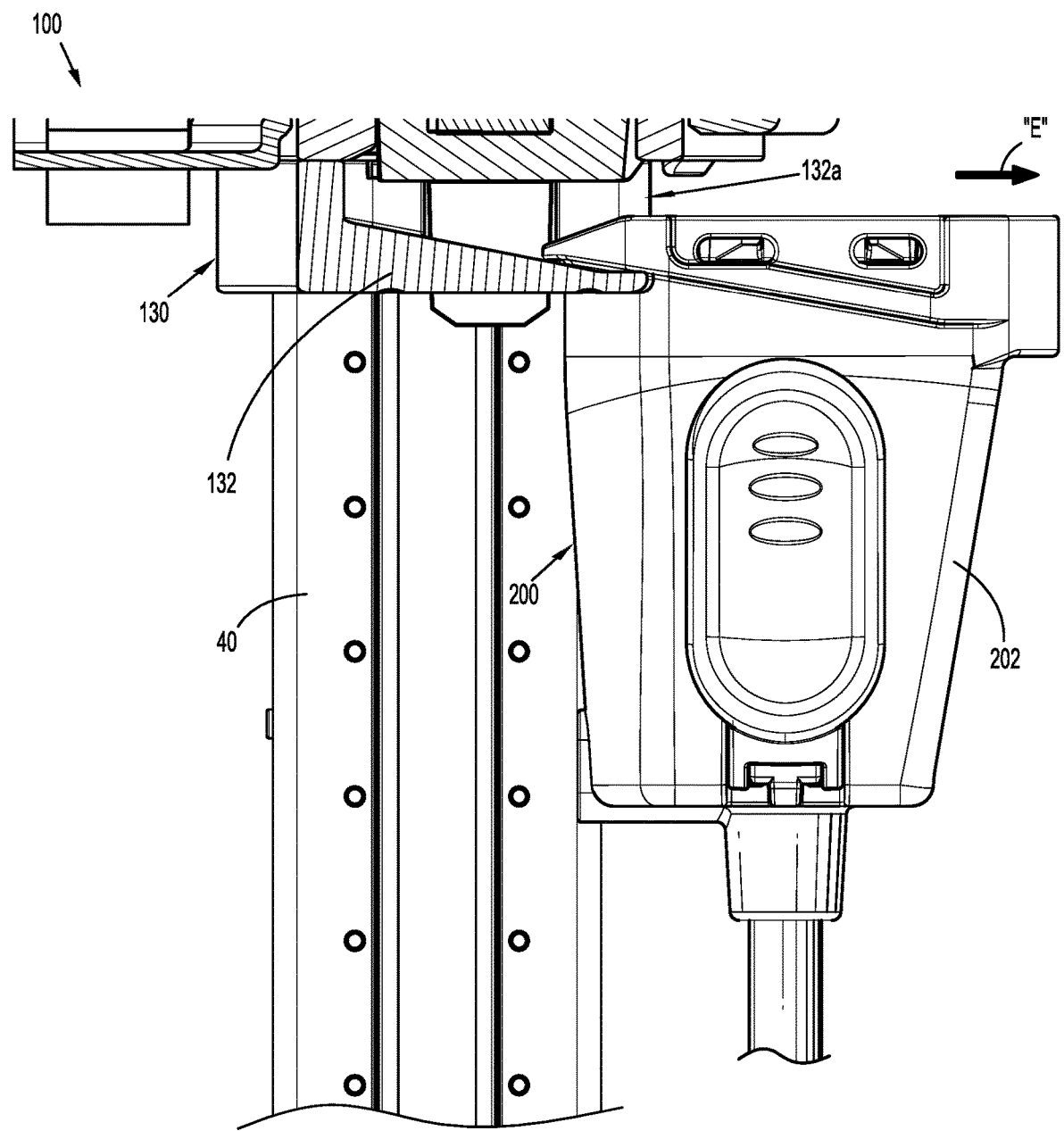

In the predetermined orientation of robotic surgical assembly 100 of robotic surgical system 1, at least a portion of robotic surgical assembly 100, such as sterile interface module 130, can be freely rotatable about longitudinal axis "L-L" of robotic surgical assembly 100 (e.g., manually to change direction of instrument release via minimal friction rotation) together with electromechanical surgical instrument 200 of robotic surgical system 1. Such rotation enables a clinician to orient lateral opening 132a of sterile interface module 130 of robotic surgical assembly 100 and electromechanical surgical instrument 200 of robotic surgical system 1 relative to slide rail 40 of robotic surgical system 1 as desired. For example, such rotation/orientation enables clinician to position robotic surgical assembly 100 and electromechanical surgical instrument 200 relative to slide rail 40 to facilitate removal of electromechanical surgical instrument 200 of robotic surgical system 1 from sterile interface module 130 of robotic surgical system 1. In the predetermined orientation of robotic surgical assembly 100, lateral opening 132a of sterile interface module 130 is clear of, or faces away from, slide rail 40 (FIG. 10) so that electromechanical surgical instrument 200 can be side-unloaded from sterile interface 130, as indicated by arrow "E," without interference from slide rail 40 as illustrated in FIGS. 11-13 (e.g., removal or attachment of electromechanical surgical instrument 200 to/from sterile interface module 130 is not blocked by slide rail 40). Robotic surgical assembly 100 can be selectively axially fixed, for example, while disposed in the freely rotatable position.

In some embodiments, the third position may be the same and/or different from the first and/or second positions.

In embodiments, controller 4 of robotic surgical system 1 can be configured to communicate with robotic surgical assembly 100 to selectively disengage and/or lock, for example, one or more gears, chains, belts (not shown) or other components within robotic surgical assembly 100 and/or slide rail 40 of robotic surgical system 1 to selectively prevent robotic surgical assembly 100 from translating axially relative to slide rail 40 while robotic surgical assembly 100 (e.g., sterile interface module 130) is disposed in the freely rotatable position. For a more detailed description of such gears, chains, or belts, reference can be made to International Patent Publication No. WO/2017/053358 previously incorporated above by reference.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

The invention claimed is:

1. A robotic surgical system, comprising:
a slide rail;
a surgical instrument defining a longitudinal axis; and
a robotic surgical assembly coupled to the slide rail and translatable along the slide rail between a first position and a second position, the robotic surgical assembly including an instrument drive unit and a sterile interface module coupled to the instrument drive unit, the surgical instrument selectively coupled to the sterile interface module, the sterile interface module rotatable with the surgical instrument about the longitudinal axis of the surgical instrument and relative to the slide rail to a predetermined orientation relative to the slide rail when the robotic surgical assembly is disposed at the first position, the surgical instrument removable from the sterile interface module when the sterile interface module and the surgical instrument are disposed in the first position.

2. The robotic surgical system of claim 1, wherein the surgical instrument includes a housing, and the sterile interface module includes a semi-annular cuff, the semi-annular cuff positioned to receive the housing of the surgical instrument to couple the surgical instrument to the sterile interface module.

3. The robotic surgical system of claim 2, wherein the semi-annular cuff defines a U-shaped opening that opens distally and laterally through the sterile interface module and is configured to slidably receive a proximal portion of the housing of the surgical instrument therein to load the proximal portion of the housing into the U-shaped opening via lateral movement of the housing of the surgical instrument relative to the semi-annular cuff.

4. The robotic surgical system of claim 3, wherein the lateral opening of the U-shaped opening is clear of the slide rail when the robotic surgical assembly is translated to the first position and rotated into the predetermined orientation.

5. The robotic surgical system of claim 1, wherein rotation of the robotic surgical assembly is robotically controlled as the robotic surgical assembly translates between the first position and the second position, and wherein at least one of the sterile interface module or the instrument drive unit becomes freely rotatable about the longitudinal axis of the surgical instrument once the robotic surgical assembly is rotated to the predetermined orientation.

6. The robotic surgical system of claim 1, further comprising a controller configured to electrically communicate with the robotic surgical assembly to enable the robotic surgical assembly to rotate to the predetermined orientation when the robotic surgical assembly is disposed in the first position.

7. The robotic surgical system of claim 6, wherein the controller is configured to selectively prevent the robotic surgical assembly from translating relative to the slide rail when the robotic surgical assembly is disposed in the first position.

8. The robotic surgical system of claim 1, wherein the first position is located at a proximal end portion of the slide rail and the second position is located at a distal end portion of the slide rail.

9. The robotic surgical system of claim 1, wherein the robotic surgical assembly is configured to automatically rotate to the predetermined orientation relative to the slide rail when the robotic surgical assembly is disposed at the first position.

10. A method for removing a surgical instrument from a robotic surgical assembly, the method comprising:

positioning the robotic surgical assembly at a predetermined location along a slide rail disposed rearwardly of the robotic surgical assembly;
rotating the surgical instrument and the sterile interface module of the robotic surgical assembly about a longitudinal axis of the surgical instrument and relative to the slide rail when the robotic surgical assembly is disposed at the predetermined location;
positioning a lateral opening of the sterile interface module so that the lateral opening is clear of the slide rail; and
unloading the surgical instrument from the lateral opening in a direction extending radially outward from the longitudinal axis.

11. The method of claim 10, wherein unloading the surgical instrument from the lateral opening includes sliding a housing of the surgical instrument along a semi-annular cuff of the sterile interface module.

12. The method of claim 10, wherein rotating the sterile interface module includes positioning the lateral opening at a predetermined orientation relative to the slide rail.

13. The method of claim 12, wherein positioning the lateral opening at a predetermined orientation relative to the slide rail includes facing the lateral opening away from the slide rail.

14. The method of claim 12, further comprising freely rotating the sterile interface module once the lateral opening is disposed in the predetermined orientation.

15. The method of claim 14, further comprising preventing the sterile interface module from axially translating along the slide rail while enabling the sterile interface module to freely rotate.

16. The method of claim 10, wherein positioning the robotic surgical assembly at the predetermined location along the slide rail includes retracting the robotic surgical assembly proximally along the slide rail to the predetermined location.

17. The method of claim 16, wherein positioning the robotic surgical assembly at the predetermined location along the slide rail includes disposing the robotic surgical assembly at a proximal-most location along the slide rail.

18. The method of claim 10, wherein rotating the surgical instrument and the sterile interface module of the robotic surgical assembly relative to the slide rail when the robotic surgical assembly is disposed at the predetermined location includes automatically rotating the surgical instrument and the sterile interface module relative to the slide rail.

19. A robotic surgical system, comprising:
a slide rail;
a surgical instrument defining a longitudinal axis; and
a robotic surgical assembly coupled to the slide rail and movable along the slide rail, the robotic surgical assembly defining a side opening configured to receive the surgical instrument for selectively coupling the surgical instrument to the robotic surgical assembly, at least a portion of the robotic surgical assembly configured to rotate with the surgical instrument about the longitudinal axis of the surgical instrument and relative to the slide rail to move the side opening between an unobstructed position and an obstructed position relative to the slide rail, wherein the slide rail prevents the surgical instrument from being uncoupled from the robotic surgical assembly when the side opening is disposed in the obstructed position, and wherein the surgical instrument is selectively removable from the robotic surgical assembly when the side opening is disposed in the unobstructed position.

* * * * *